United States Patent [19]

Bashour

[11] Patent Number: 4,558,699

[45] Date of Patent: Dec. 17, 1985

[54] METHOD OF AND APPARATUS FOR RESTRICTING THE PASSAGE OF FOOD THROUGH THE STOMACH

[76] Inventor: Samuel B. Bashour, 2504 Summit, Irving, Tex. 75062

[21] Appl. No.: 455,025

[22] Filed: Jan. 3, 1983

[51] Int. Cl.⁴ ............................................. A61B 17/08
[52] U.S. Cl. .................................................. 128/346
[58] Field of Search ............................... 128/325, 346

[56] References Cited

U.S. PATENT DOCUMENTS

| | | | |
|---|---|---|---|
| 1,982,207 | 11/1934 | Furniss | 128/346 |
| 2,686,520 | 8/1954 | Jarvis et al. | 128/346 |
| 3,746,002 | 7/1973 | Haller | 128/346 X |
| 4,227,730 | 10/1980 | Alexander et al. | 128/346 X |
| 4,458,681 | 7/1984 | Hopkins | 128/346 |

Primary Examiner—Dalton L. Truluck
Attorney, Agent, or Firm—Michael A. O'Neil

[57] ABSTRACT

The passage of food through a stomach (S) is restricted by clamping an apparatus (10) around the stomach (S). The apparatus (10) comprises cooperating jaws (12, 14) having stomach engaging surfaces (22, 24). The stomach engaging surfaces (22, 24) define a relatively open area (26) which permits the passage of food therethrough at a restricted rate. The stomach engaging surfaces (22, 24) further define relatively closed areas (28, 30) which prevent the passage of food therethrough. The apparatus (10) is secured in place on the stomach (S) by cooperating teeth (36) which engage the stomach wall, and by sutures formed between the stomach wall and apertures (38, 40, 42) formed in the jaws (12, 14).

18 Claims, 3 Drawing Figures

METHOD OF AND APPARATUS FOR RESTRICTING THE PASSAGE OF FOOD THROUGH THE STOMACH

TECHNICAL FIELD

This invention relates generally to the control of obesity, and more particularly to a method of and apparatus for clamping the stomach to restrict the passage of food therethrough.

BACKGROUND AND SUMMARY OF THE INVENTION

Physicians engaged in the treatment of obesity frequently see patients weighing up to 450 pounds or more. In the past, diverse techniques have been employed to achieve weight loss in these patients, with varying degrees of success. For example, phsychological techniques such as hypnosis, behavior modification, etc. have been used, sometimes with very substantial benefit to the patient, i.e., substantial and continuing weight loss, and sometimes with little or no benefit whatsoever. Another weight loss technique that has been frequently employed involves the use of various drugs to suppress appetite. In many instances the side effects resulting from the use of appetite suppressing drugs are such that the administration thereof must be discontinued.

Various surgical techniques have also been employed in achieving weight loss in obese patients. In accordance with one such technique, the stomach is resectioned to substantially reduce its volume. This causes the patient to achieve a feeling of being "full" after consuming substantially less food than previously. It will be appreciated that the resectioning of the stomach is a major surgery involving not only considerable risk to the patient, but also substantial cost due to this requirement of an extended stay in the hospital for recovery from the surgery, etc.

Another surgical technique for achieving weight loss involves the use of staples, whereby the upper portion of the stomach is separated from the lower portion. Although this technique has generally proven successful, some problems have been encountered. For example, in at least some instances the staples have been known to pull loose which may necessitate that the surgery be repeated if continued weight loss is to be achieved.

The present invention comprises a method of and apparatus for achieving weight loss in obese patients which overcomes the foregoing and other difficulties long since experienced with the prior art. In accordance with the broader aspects of the invention, a clamp is secured around the exterior of the stomach and serves to substantially restrict the passage of food therethrough. In this manner substantial weight loss is achieved without encountering the difficulties associated with prior art techniques.

In accordance with more specific aspects of the invention, apparatus for restricting the passage of food through the stomach includes cooperating jaws having opposed stomach engaging surfaces. The stomach engaging surfaces define at least one relatively open area which permits the passage of food through the portion of the stomach received therein, and at least one relatively closed area which prevents the passage of food through the portion of the stomach received therein. Structure is provided for securing the jaws against movement relative to the stomach.

In accordance with still more specific aspects of the invention, the relatively open area defined by the stomach engaging surfaces of the jaws is circular in shape and is characterized by a diameter of about 1.25 centimeters. The relatively open area is centrally located, and two relatively closed areas extend outwardly from the relatively open area. Each of the relatively closed areas has a plurality of interlocking teeth for gripping the portion of the stomach received therein. In addition, opposed sets of relatively sharp teeth engage on opposite sides of the stomach to prevent movement of the jaws relative thereto. Apertures are provided in the jaws for receiving sutures to further secure the jaws against movement relative to the stomach.

In accordance with still other aspects of the invention, the jaws are hingedly secured one to the other. Locking structure is provided for securing the jaws against pivotal movement with respect to one another. The jaws are preferably formed from a plastic material which does not adversely effect either the stomach wall or the interior of the abdominal cavity. Structure is provided for rendering at least one of the jaws opaque to X-ray diagnostic techniques so that the apparatus may be observed by means of X-ray.

DESCRIPTION OF THE DRAWINGS

A more complete understanding of the invention may be had by reference to the following Detailed Description when taken in conjunction with the accompanying Drawings, wherein.

DETAILED DESCRIPTION

Figure 2:
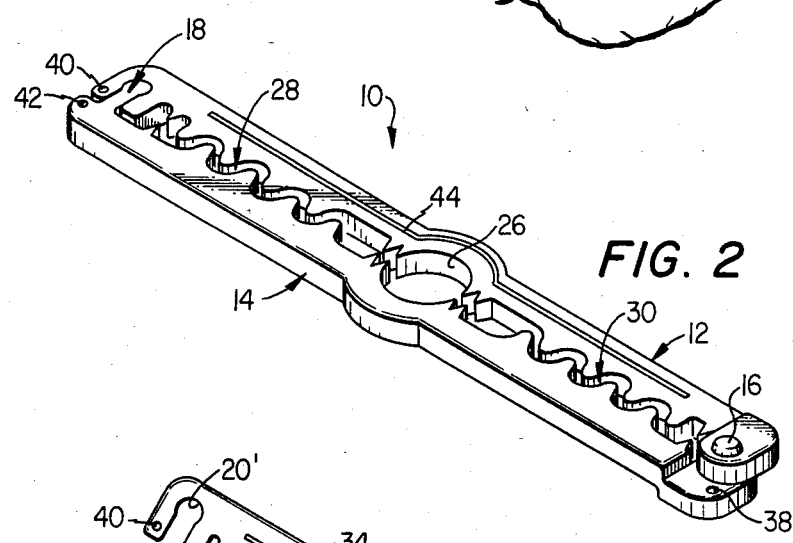
FIG. 2 is a perspective view of the apparatus of the invention.
Figure 3:
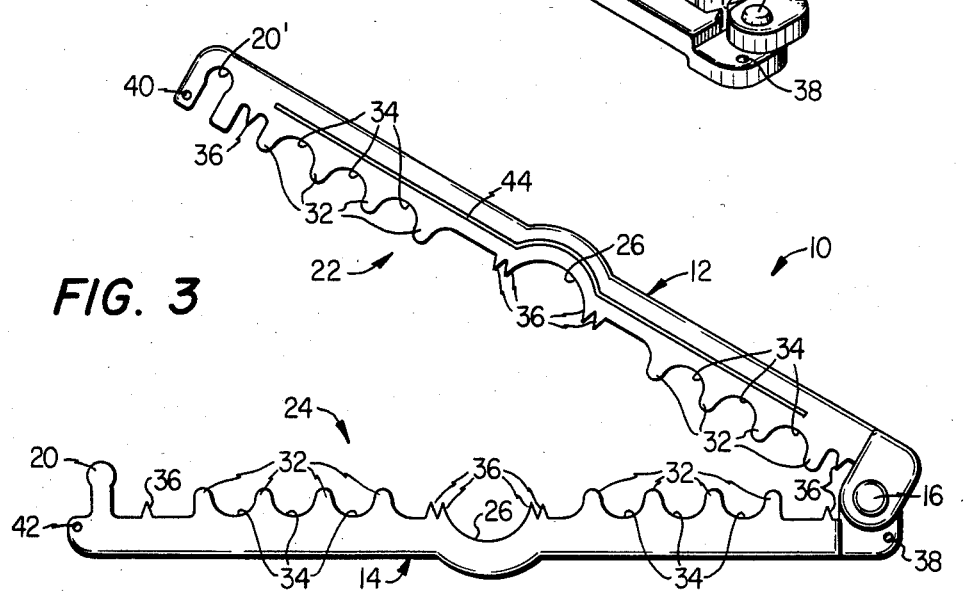
FIG. 3 is a front view of the apparatus of the invention.

Referring now to the Drawings, and particularly to FIGS. 2 and 3 thereof, there is shown an apparatus for restricting the passage of food through a stomach 10 incorporating the preferred embodiment of the invention. The apparatus 10 is comprised of cooperating jaws 12 and 14. A pivot pin 16 hingedly interconnects the jaws 12 and 14 and supports the jaws 12 and 14 for pivotal movement with respect to one another. It will be understood that the jaws 12 and 14 may be hingedly interconnected by apparatus other than a pivot pin, for example, a flexible hinge may be used to pivotally interconnect the jaws 12 and 14.

The apparatus 10 includes a locking mechanism 18 situated at the opposite ends of the jaws 12 and 14 from the pivot pin 16. The locking mechanism 18 comprises a latching member 20 projecting from the jaw 14 and a latching member receiving aperture 20' formed in the jaw 12. In the operation of the locking mechanism 18, the latching member 20 is receivable in the locking member receiving aperture 20' to secure the jaws 12 and 14 against pivotal movement relative to each other. It will be said that other types of locking mechanisms may be utilized in the practice of the invention, if desired.

The cooperating jaws 12 and 14 of the apparatus 10 comprise opposed stomach engaging surfaces 22 and 24, respectively. The surfaces 22 and 24 define a centrally located, relatively open area 26. The relatively open area 26 defined by the surfaces 22 and 24 is circular in shape and is characterized by a diameter of approximately 1.25 centimeters. It will be understood that the relatively open area 26 may have other shapes and other dimensions in accordance with the particular applications of the invention.

The purpose of the relatively open area 26 is to permit the passage of food through a stomach portion received therein, but a substantially reduced rate. This causes the patient to feel "full" after consuming substantially less food than would otherwise be the case. In this manner the intake of calories is reduced and weight loss is achieved.

The surfaces 22 and 24 of the cooperating jaws 12 and 14 further define two relatively closed areas 28 and 30 which extend outwardly in opposite directions from the relatively open area 26. The relatively closed areas 28 and 30 defined by the surfaces 22 and 24 are comprised of a plurality of interlocking teeth 32. That is, the teeth 32 of the jaw 12 are each positioned in alignment with and are each adapted for movement into a tooth receiving aperture 34 of the jaw 14. Likewise, each tooth 32 of the jaw 14 is positioned in alignment with and is adapted for movement into a tooth receiving aperture 34 of the jaw 12.

The purpose of the relatively closed portions 28 and 30 defined by the stomach engaging surfaces 22 and 24 of the apparatus 10 is to prevent the passage of food through stomach portions received therein without inflicting damage on the stomach wall. To this end the teeth 32 defining the relatively closed portions 28 and 30 are relatively wide and dull in shape and are positioned for entry into the apertures 34 so as to securely grip the stomach wall without imposing undue stress thereon.

The apparatus 10 further includes structure for preventing movement of the jaws 12 and 14 relative to a stomach gripped therebetween. The jaws 12 and 14 are provided with sets of opposed teeth 36. The teeth 36 are relatively narrow and sharp as compared with the teeth 32. Even more importantly, the teeth 36 of the jaw 12 are positioned directly opposite corresponding teeth 36 of the jaw 14. The function of the teeth 36 of the apparatus 10 is to engage the stomach wall in such a way as to prevent relative movement between the jaws 12 and 14 and a stomach gripped therein.

The structure of the apparatus 10 for preventing relative movement between the jaws 12 and 14 in a stomach grip therein further includes a plurality of suture receiving apertures 38, 40 and 42. In the practice of the invention, sutures are applied between the wall of a stomach received between the jaws 12 and 14 and the apertures 38, 40 and 42 to prevent movement of the jaws 12 and 14 relative to the stomach. In addition, sutures may be wound through the apertures 40 and 42 as an aid to the locking mechanism 18 to prevent pivotal movement of the jaws 12 and 14 relative to each other.

The jaws 12 and 14 comprising the apparatus 10 are preferably formed from a material which does not adversely effect either the stomach wall or the interior of the abdominal cavity. In the practice of the invention, it has been found that nylon may be used in the fabrication of the jaws 12 and 14 of the apparatus 10. Other plastic materials commonly utilized in the manufacture of medical appliances may also be used in the practice of the invention. In addition, various metals, for example, stainless steel, may be utilized in the practice of the invention.

Those skilled in the art will appreciate the fact that in the use of the apparatus 10 it is frequently desired to examine the patient by means of X-ray, sonography or other forms of diagnostic techniques. Since nylon and similar plastic materials are often found to be quite transparent to such radiation, one or both of the cooperating jaws comprising the apparatus 10 may be provided with an insert 44 which is opaque to X-ray radiation of the type utilized to pass through the tissue of a patient to form visually perceptible images thereof. The insert 44 need not comprise a unitary structure, but instead may comprise a series of discreet segments, if desired.

Figure 1:
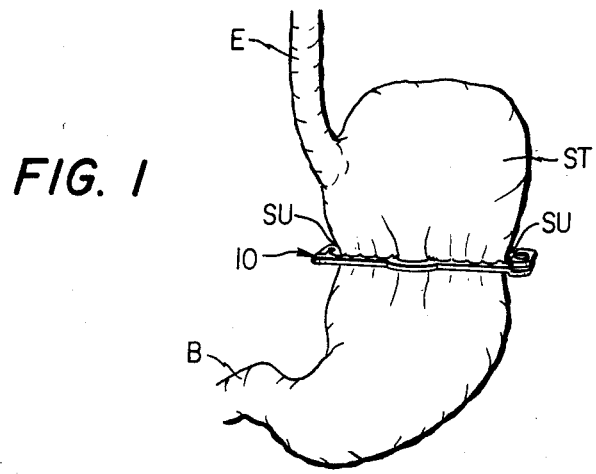
FIG. 1 is a diagrammatic illustration of the method and apparatus of the invention.

Referring now to FIG. 1, the method and apparatus of the invention are shown. Stomach ST extends between the lower end of esophagus E and the upper end of small bowel B. Although the invention is illustrated in the Drawings in conjunction with a human stomach, it will be understood that the invention is equally applicable to other animals in the event that the restriction of the passage of food through the stomach thereof is considered necessary or desirable.

In the practice of the invention the cooperating jaws 12 and 14 comprising the apparatus 10 are initially opened sufficiently to receive the stomach ST therebetwee the stomach engaging surfaces 22 and 24. The jaws 12 and 14 are then positioned relative to the external walls of the stomach ST. Preferably, the apparatus 10 is positioned relatively close to the upper end of the stomach ST. It will be understood, however, that the precise positioning of the apparatus 10 is not critical to the practice of the invention.

After the apparatus 10 has been properly positioned relative to the stomach ST, the jaws 12 and 14 are closed to securely grip the stomach ST therebetween. The locking mechanism 18 is actuated to prevent pivotal movement of the jaws 12 and 14 relative to one another. That is, the locking member 20 is engaged with the locking member receiving aperture 20' to secure the jaws 12 and 14 in place. At this point the opposed teeth 36 of the jaws 12 and 14 engage the stomach walls to prevent the jaws 12 and 14 from movement relative to the stomach ST.

Thereafter sutures are extended between the stomach wall and the apertures 38, 40 and 42 to further secure the jaws 12 and 14 against movement relative to the stomach ST. The sutures are also extended between the apertures 40 and 42. In this manner the sutures cooperate with the locking mechanism 18 to prevent the jaws 12 and 14 from pivotal movement relative to one another. The sutures are omitted in FIG. 1 for clarity, but are indicated at points SU.

The purpose in clamping the apparatus 10 around the exterior of the stomach ST is to substantially restrict the passage of food through the stomach. The relatively open area 26 defined by the stomach engaging surfaces 22 and 24 of the cooperating jaws 12 and 14 of the apparatus 10 allows food to pass through the stomach ST, but at a substantially reduced rate relative to that which would be afforded by the stomach ST in its unrestricted condition. This causes the patient to feel "full" after consuming substantially less food than would normally be the case. In this manner the use of the present invention is highly beneficial in causing weight loss in obese patients, but does not result in the complications which have heretofore been encountered in the practice of techniques such as stomach resectioning or stomach stapling.

More specifically, the relatively open area 26 defined by the stomach engaging surfaces 22 and 24 of the jaws 12 and 14 of the apparatus 10 permits the flow of food through the portion of the stomach received therein at a restricted rate. The relatively closed areas 28 and 30 defined by the stomach engaging surfaces 22 and 24 of the jaws 12 and 14 prevent the passage of food therethrough. Relative movement between the jaws 12 and 14 comprising the apparatus 10 is prevented by engagement by the opposed teeth 36 with the wall of the stomach gripped therebetween, and in addition by sutures formed between the stomach walls and the apertures 38, 40 and 42. Disengagement of the jaws 12 and 14 from the stomach wall is prevented by the locking mechanism 18 and by sutures formed through the apertures 40 and 42. The insert 44 allows observation of the apparatus 10 by means of X-rays or similar techniques.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

I claim:
1. An extended duration implantation apparatus for restricting the passage of food through a stomach comprising:
   first and second cooperating jaws having opposed stomach wall engaging surface for clamping a stomach therebetween, the jaws being connected for co-planar pivotal movement with respect to each other;
   said opposed stomach wall engaging surfaces of the jaws defining at least one relatively open area for permitting the passage of food through the portion of the stomach received therein and at least one relatively closed area for preventing the passage of food through the portion of the stomach received therein, the relatively closed area of the opposed stomach wall engaging surfaces of the jaws further characterized by a plurality of matingly engagable contours for gripping a portion of the stomach therebetween whereby said jaws are prevented from movement relative to the stomach;
   means for preventing movement of the jaws relative to a stomach clamped therebetween;
   the first jaw being of a one-piece construction and having and an integral latching member extending from the unhinged end thereof towards the second jaw, a portion of the latching member including a locking mechanism;
   the second jaw having a receptacle for receiving the latching member of the first jaw and for engaging the locking mechanism of the latching member when the latching member is fully inserted therein; and
   wherein the latching member, when fully inserted in the receptacle of the second jaw, maintains a predetermined distance of separation between the stomach engaging surfaces of the jaws throughout the relatively closed area defined thereby sufficient to substantially prevent traumatizing stomach tissue secured between the jaws.

2. The apparatus according to claim 1 wherein the relatively closed area of the opposed stomach wall engaging surfaces of the jaws is further characterized by a plurality of matingly engageable contours for gripping a portion of the stomach therebetween.

3. The apparatus according to claim 1 wherein the movement preventing means includes at least one set of teeth formed on the jaws for engaging the opposite sides of the stomach to prevent movement of the jaws relative to the stomach.

4. The apparatus according to claim 1 wherein the movement preventing means includes at least one aperture formed through at least one of the jaws for receiving a suture to secure the jaws to the stomach and thereby prevent movement of the jaws relative to the stomach.

5. The apparatus according to claim 1 wherein the relatively open area of the stomach wall engaging surfaces of the cooperating jaws is substantially centrally disposed, and wherein the opposed stomach wall engaging surfaces define two relatively closed areas for preventing the passage of food through the portion of the stomach received therein, said relatively closed areas extending in opposite directions from the relatively open area.

6. The apparatus according to claim 1 wherein the relatively open area defined by the opposed stomach wall engaging surfaces of the cooperating jaws is circular in shape and is characterized by a diameter approximately 1.25 centimeters.

7. The apparatus according to claim 1 wherein each of the relatively closed area defined by the stomach wall engaging surfaces of the cooperating jaws comprises a plurality of interlocking teeth formed on the jaws and comprising the stomach engaging surfaces thereof for gripping the portion of the stomach received therein, and wherein the movement preventing means is characterized by at least one set of opposed, relatively pointed teeth formed on the jaws for engaging the opposite sides of the stomach and thereby preventing movement of the jaws relative to the stomach.

8. The apparatus according to claim 1 further characterized by means mounted on at least one of the jaws which is opaque to electro-magnetic radiation.

9. The apparatus according to claim 1, wherein the locking mechanism of the latching member includes a portion of the latching member having a greater cross-sectional area relative to the remainder of the latching member.

10. Apparatus for an extended duration implantation around a human stomach for restricting the passage of food through the stomach and thereby effecting weight loss in an obese patient comprising:
   first and second cooperating jaws having opposed stomach wall engaging surfaces for clamping a stomach therebetween, the jaws being connected for pivotal movement with respect to each other;
   said opposed stomach wall engaging surfaces defining a centrally located relatively open area having a substantially circular shape and a diameter of about 1.25 centimeters for permitting the passage of food through the portion of the stomach received therein and two relatively closed areas extending in opposite directions from the open area for preventing the passage of food through the portion of the stomach received therein, the relatively closed area of the opposed stomach wall engaging surfaces of the jaws further characterized by a plurality of matingly engagable contours for gripping a portion of the stomach therebetween whereby said jaws are prevented from movement relative to the stomach;

means situated at first ends of the cooperating jaws for supporting the jaws for co-planar pivotal movement relative to one another;

the first jaw being of a one-piece construction and having an integral latching member extending from the free end thereof toward the second jaw, a portion of the latching member including a locking mechanism;

the second jaw having a receptacle for receiving the latching member of the first jaw and for engaging the locking mechanism of the latching member when the latching member is fully inserted therein;

wherein the latching member, when fully inserted in the receptacle of the second jaw, maintains a predetermined distance of separation between the stomach engaging surfaces of the jaws throughout the relatively closed areas defined thereby sufficient to substantially prevent traumatizing stomach tissue secured between the jaws; and means for preventing movement of the jaws relative to a stomach clamped therebetween.

11. The apparatus according to claim 10 wherein each of the relatively closed areas defined by the stomach engaging surfaces of the cooperating jaws is further characterized by a plurality of interlocking teeth for gripping the portion of the stomach received therein.

12. The apparatus according to claim 10, wherein the locking mechanism of the latching member includes a portion of the latching member having a greater cross-sectional area relative to the remainder of the latching member.

13. A method of restricting the passage of food through a stomach and thereby effecting weight loss in an obese patient comprising:

providing first and second cooperating jaws with opposed matingly engagable contoured stomach engaging surfaces, the jaws being connected for co-planar pivotal movement with respect to each other, at least the first jaw having a one-piece construction;

clamping the cooperating jaws around the outside of a stomach with the stomach engaging jaws thereof positioned in engagement with the opposite sides of the stomach and located to substantially restrict the passage of food through the stomach;

securing the cooperating jaws against movement relative to the stomach clamped therebetween;

providing the first jaw with an integral latching member extending from the free end thereof towards the second jaw, a portion of the latching member including a locking mechanism;

providing the second jaw with a receptacle for receiving the latching member of the first jaw and for engaging the locking mechanism of the latching member when the latching member is fully inserted therein;

maintaining a predetermined distance of separation, by means of the latching member, between the stomach engaging surfaces of the jaws sufficient to substantially prevent traumatizing stomach tissue clamped therebetween; and maintaining the first and second cooperating jaws engaged around the stomach for an extended period of time.

14. The method according to claim 13 further characterized by providing the cooperating jaws with stomach engaging surfaces defining at least one relatively open area for permitting the passage of food through the portion of the stomach received therein and at least one relatively closed area for preventing the passage of food through the portion of the stomach received therein.

15. The method according to claim 13 further characterized by providing stomach engaging surfaces defining a relatively open area therebetween which is circular in shape and characterized by a diameter of about 1.25 centimeters.

16. The method according to claim 13 wherein the step of securing the jaws against movement relative to the stomach clamped therebetween is further characterized by providing the cooperating jaws with at least one set of opposed, relatively pointed teeth for gripping the stomach therebetween and thereby preventing movement of the jaws relative to the stomach.

17. The method according to claim 13 wherein the step of securing the jaws against movement relative to a stomach clamped therebetween is further characterized by:

providing the cooperating jaws with suture receiving apertures; and forming sutures between the stomach and the suture receiving apertures of the jaws to secure the jaws against movement relative to the stomach.

18. The method according to claim 13 further characterized by providing the cooperating jaws with opposed stomach engaging surfaces defining a centrally located relatively open area and further defining two relatively closed areas which extend outwardly from the centrally located relatively open area, the relatively open area being circular in shape and characterized by a diameter of about 1.25 centimeters.

* * * * *